United States Patent [19]

Maldonado et al.

[11] 3,997,399
[45] Dec. 14, 1976

[54] FERMENTATION PROCESS FOR THE PRODUCTION OF CITRIC AND ISOCITRIC ACIDS

[75] Inventors: Paul Maldonado, Saint Symphorien d'Ozon; Max Charpentier, Montesson, both of France

[73] Assignee: Institut Francais du Petrole, des Carburants et Lubrifiants et Entreprise de Recherches et d'Activities Petrolieres Elf, Rueil-Malmaison, France

[22] Filed: May 14, 1975

[21] Appl. No.: 577,446

[30] Foreign Application Priority Data

May 15, 1974 France .............................. 74.16911

[52] U.S. Cl. .................................. 195/29; 195/28 R
[51] Int. Cl.² ........................................... C12B 1/00
[58] Field of Search ................. 195/28 R, 36 R, 29, 195/37, 47, 30, 82, 114

[56] References Cited

FOREIGN PATENTS OR APPLICATIONS 1,204,635    9/1970    United Kingdom ................ 195/30

*Primary Examiner*—A. Louis Monacell
*Assistant Examiner*—R. B. Penland
*Attorney, Agent, or Firm*—Eyre, Mann, Lucas & Just

[57] ABSTRACT

The invention relates to a process for the production of citric and osocitric acids by a culture of a diploid *Candida Lipolytica* yeast in a nutrient medium containing substances which are sources of carbon, nitrogen, and mineral compounds, the medium containing thiamin in a concentration in excess of 200 micrograms per liter.

4 Claims, No Drawings

FERMENTATION PROCESS FOR THE PRODUCTION OF CITRIC AND ISOCITRIC ACIDS

The present invention relates to a process for the production of citric and isocitric acids by a culture of a diploid *Candida Lipolytica* yeast.

A process for the production of citric and isocitric acids by a culture of a *Candida Lipolytica* yeast has already been described; this process is characterised in that this culture is effected in the presence of cyanoacetic acid or a derivative thereof this additive having the effect of substantially increasing the production of the acid during this culture.

A process has been described for producing new diploid strains of *Candida Lipolytica*, and it was thus found that the culture of these new diploid strains led to the production of substantial amounts of alpha-ketoglutaric acid. The addition of cyanoacetic acid or a derivative thereof to the culture medium described did not make it possible to obtain substantial amounts of citric and isocitric acids.

A systematic study of the constitution of the culture medium of these diploid strains of *Candida Lipolytica* made it possible to find a process permitting the orientation of the production of the culture in the direction of citric and isocitric acids.

According to one aspect of the present invention there is provided a process for the production of citric and isocitric acids by a culture of a diploid *Candida Lipolytica* yeast in a nutrient medium containing substances which are sources of carbon, nitrogen, and mineral compounds, the medium containing thiamin in a concentration in excess of 200 micrograms per liter and such that citric and isocitric acids are produced.

It was previously known that culture mediums should have a determined pH, which is between 2 and 7 and preferably between 3 and 6. As the production of citric and isocitric acids progresses the pH of the culture medium will progressively decrease, and it is important to maintain it within the above limits by adding a suitable base to the culture medium. Ammonia is generally used for this purpose. Thus in a process according to the present invention it is preferable that the medium has a pH between 2 and 7, the pH of the medium being maintained by addition of a non-nitrogen containing base, such as sodium hydroxide or potassium hydroxide. Thus the pH of the medium may between 3 and 6. The non-nitrogen containing base may be sodium hydroxide or potassium hydroxide. When this is done, the yield of citric and isocitric acids from the culture is considerably increased.

Finally, in the process of the invention it is possible and desirable to increase still further the yield of citric or isocitric acid. Thus the culture may be effected in the presence of cyanoacetic acid or of a derivative thereof.

Preferably, the medium contains up to a few milligrams per liter, for example, 10 milligrams per liter, of thiamin.

According to a further aspect of the present invention there is provided citric and isocitric acids when produced by the method recited above.

The yeast used in the process of the present invention is a "diploid *Candida Lipolytica* yeast". A yeast of this kind can be obtained by means of the following operations:

in a first stage two haploid germ strains of *Candida Lipolytica* of opposite signs are cultivated separately, this culture being effected in media rich in assimilable hydrocarbon substrate;

in a second stage the two cultures are brought together and cultivated in a medium poor in assimilable hydrocarbon substrate - this culture brings about the appearance of colonies of diploids;

in a third stage these colonies of diploids are treated with a mutagen in order to stabilise them.

In this process for the preparation of diploid yeasts the term "medium rich in assimilable hydrocarbon substrate" is applied to a medium which contains at least 10 grams per liter of assimilable hydrocarbon substrate, while the expression "media poor in assimilable hydrocarbon substrate" means those which contain less than about 0.5 gram per liter of the hydrocarbon substrate.

The mutagenesis of the third stage of the process may be effected in a known manner by utilising a chemical agent (such as for example nitrosomethylguanidine nitrosomethylurethane) or by radiation (for example X-rays and ultraviolet rays).

The diploid *Candida Lipolytica* yeast is cultivated as described hereinbelow. The culture medium has a hydrocarbon substrate.

This hydrocarbon substrate is preferably composed of paraffinic hydrocarbons, that is to say either an n-paraffin alone or a n-paraffinic cut.

Although the use of an n-paraffin by itself makes it possible to obtain better results, it is generally preferred, essentially for reasons of cost, to work with an n-paraffinic cut usually containing from 5 to 22 carbon atoms per molecule.

In addition to the assimilable hydrocarbon substrate the culture medium contains the usual elements necessary for fermentation, that is to say a source of nitrogen such as ammonium chloride, ammonium sulphate, ammonium nitrate, ammonium acetate, ammonium phosphate, or ammonium carbonate.

The mineral compounds which can be added to the culture medium may be magnesium sulphate, phosphoric acid, potassium hydroxide, sodium phosphate, potassium phosphate, sodium hydroxide, manganese sulphate, manganese chloride, iron sulphate, manganese carbonate, manganese chloride, sodium carbonate, or potassium carbonate.

In addition, it may be necessary to add certain essential nutrient substances to the culture medium, such as vitamins, nicotinic acid, biotin, etc.

In certain cases, the addition of a surfactant, such as a tween, a span, or a triton, may be effective in increasing the yield of product.

Fermentation is preferably effected at a temperature between 24° C and 34° C and with an acid pH between 2 and 7, preferably between 3 and 6.

The culture is effected in the presence of air, and the culture medium is vigorously agitated by any suitable means in order to disperse the hydrocarbon substrate as much as possible.

Before the actual fermentation process is effected, the selected strains of diploid *Candida Lipolytica* yeast are subjected to preculture intended to bring about growth, thus enabling the fermenter to be seeded under good conditions of cellular concentration (for example $10^7$ cells/ml).

The influence of thiamin concentration (the thiamin being for example supplied in the form of thiamin hydrochloride) in the culture medium was demonstrated by making comparative tests, in which the same strain of diploid *Candida Lipolytica* yeast was cultivated on the same culture medium containing different concentrations of thiamin:

when the concentration of thiamin in the culture medium is low (between 0.01 and 10 micrograms per liter) the culture does not excrete citric or isocitric acid, but only alpha-ketoglutaric acid.

when the concentration of thiamin is between 10 and substantially 200 micrograms per liter, no excretion of acids — either citric acids or alpha-ketoglutaric acid — is observed.

when the concentration of thiamin exceeds 200 micrograms per liter, the excretion of citric and isocitric acids is observed, but no production of alpha-ketoglutaric acid.

This shows the advantageous specific action of the concentration of thiamin in the culture medium.

The following non-limitative examples illustrate the invention.

EXAMPLE 1

Production of diploids and description of strains

Two strains of *Candida Lipolytica*, isolated from samples of earth were considered, one being a haploid of signs A (IFP29 - ATCC No. 20460) and the other a haploid of sign B (ELF 30 - ATCC No. 20461).

1st stage.

These strains were cultivated separately for 24 hours at 25° C on a presporulation medium A (rich medium), whose composition is as follows:

Glucose — 20 g
$(NH_4)_2SO_4$ — 2 g
$KH_2PO_4$ — 2 g
Yeast extract — 10 g
Bacto Agar Difco — 20 g
Distilled water — 1000 g 2nd stage.

A suspension of from $10^7$ to $10^8$ cells/ml was formed in distilled water for each of the strains. 1 ml of each suspension was taken; vigorous mixing was effected, and 0.1 ml of this mixture was taken and deposited in an inclined gelose tube of a vegetable juice sporulation medium B prepared in the following manner: 350 ml of a broth of eight different vegetables supplying the energy equivalent of about 2 g/l of glucose was adjusted to a pH of 6.8 by means of KOH 1 N, and 7 g of dry yeast IFP 29 was added thereto. The mixture was heated to 100° C for 20 minutes on a water bath, and then filtered through paper. The filtrate was adjusted to a pH of 6.8 as previously, and its volume was doubled by adding the same volume of tap water. After the addition of Bacto Agar Difco 2%, the medium was sterilised in 10 cc tubes for 15 minutes at 110° C.

The culture on medium B, where some asci are forming, was suspended in 10 ml of distilled water subjected to sonic treatment for 3 minutes at 0° C (Mullard MSE Disintegrator) amd was spread out on medium B in a Petri dish with the appropriate dilution. After from 7 to 15 days some colonies of diploids appeared on this medium. These colonies were very rich in asci (about 50% in relation to the vegetable cells). They were taken up and sorted out on a medium rich in yeast extract (yeast extract, 0.5%, glucose 2%, Agar Difco 2%). The large colonies selected were diploids, which can be cultivated as such without sporulation on a full or rich medium, during a number of subcultures. The diploid strain obtained in this manner has been designated $D_{18}$.

From the $D_{18}$ diploid strain a series of colonies was isolated after UV mutagenesis ($10^7$ cells of diploid stain $D_{18}$ irradiated for 1 minute at 2000 ergs/mm$^2$/minute). All these colonies have very low fertility. From these, four strains derived from diploid strain $D_{18}$ were selected, which after 15 days and 3 weeks on the poor medium B no longer formed asci (absence of sporulation). These four strains were respectively designated D 1802, D 1805 (ATCC No. 20390), D 1806, and D 1807.

By ADN quantity determination by Burton's method (*Biochemical Journal* 62, 315–323, 1956) and micrometer measurement of cellular sizes, it was observed that these strains remain close to diploid strain $D_{18}$.

| Strains | $\mu$ g of desoxyadenosine by $10^8$ cells |
|---|---|
| IFP 29 | 0.58 |
| ELF 30 | 0.65 |
| D 18 | 0.89 |
| D 1802 | 0.88 |
| D 1805 | 1.05 |
| D 1806 | 1.27 |
| D 1807 | 1.26 |

Cellular sizes

The cells have the form of ellipsoids with the following characteristics:

| Strains | Maximum axis ($\mu$) | Minimum Axis ($\mu$) |
|---|---|---|
| IFP 29 | 4.5 | 2.7 |
| ELF 30 | 4.6 | 2.9 |
| D 18 | 7.7 | 4.2 |
| D 1802 | 7.8 | 2.9 |
| D 1805 | 12.1 | 6.3 |
| D 1806 | 8.3 | 4.4 |
| D 1807 | 11.3 | 5.0 |

Form of colonies on hydrocarbon gelose medium

Round, curved, granulated, glossy, pale yellow. Assimilation of substrates (identical for the various strains)

| | | |
|---|---|---|
| Sucrose | — | negative |
| Maltose | — | negative |
| Galactose | — | negative |
| Glucose | + | positive |
| Raffinose | | low |
| C9 to C22 paraffins | + | positive |

EXAMPLE 2

Preparation of the inoculum

From a gelose tube containing diploid cells of *Candida Lipolytica* yeast a 100 ml flask was seeded, the flask containing 20 ml of a liquid preculture medium of the following composition:

| | |
|---|---|
| $KH_2PO_4$ | 3.4 g/l |
| $Na_2HPO_4$, 12 $H_2O$ | 1.7 g/l |
| $MgSO_4$, 7 $H_2O$ | 0.7 g/l |
| $(NH_4)_2SO_4$ | 4 g/l |
| $CaCl_2$ | 0.1 g/l |
| $FeSO_4$, 7 $H_2O$ | 2 mg/l |
| $CuSO_4$, 5 $H_2O$ | 5 $\mu$g/l |

-continued

| | |
|---|---|
| $H_3BO_3$ | 10 μg/l |
| $Mn\ SO_4, 7\ H_2O$ | 10 μg/l |
| $ZnSO_4, 7\ H_2O$ | 10 μg/l |
| $(NH_4)_6\ Mo_7\ O_{24}, 4\ H_2O$ | 100 μg/l |
| $Co\ (NO_3)_2, 6\ H_2O$ | 10 μg/l |
| Yeast extract | 100 mg/l |
| Tap water | to make 1 liter |
| n-paraffin cut $C_{12} - C_{20}$ | 15 g/l |

Preparation of the following preculture

After incubation of 36 hours at 30° C on an agitation table adjusted to the speed of 140 rpm, 10 ml of the inoculum were used to seed 200 ml of a nutrient medium contained in a 1.5-liter Fernbach flask and having the following composition:

| | |
|---|---|
| $KH_2PO_4$ | 2 g/l |
| $MgSO_4, 7\ H_2O$ | 1 g/l |
| $NH_4NO_3$ | 2.5 g/l |
| $CaCO_3$ | 20 g/l |
| $Fe\ SO_4, 7\ H_2O$ | 0.2 g/l |
| $Mn\ SO_4, 7H_2O$ | 26 mg/l |
| Yeast extract | 100 mg/l |
| Tap water to make | 1 liter |

Preparation of the fermentation

After incubation for 36 hours under the same conditions as before, this medium served as inoculum to seed a 2.5-liter fermenter containing 1.5 liter of a culture medium of the following composition:

| | g/100 ml of medium |
|---|---|
| KOH (85%) | 0.165 |
| $H_3PO_4$ (42.5%) | 0.680 |
| $MgCl_2, 6\ H_2O$ | 0.170 |
| $NH_4NO_3$ | 0.5 |
| $FeSO_4, 7\ H_2O$ | 0.04 |
| $MnSO_4, H_2O$ | 0.005 |
| Thiamin hydrochloride | $10^{-4}$ |
| Cyanoacetic acid 0.01, added after 24 hours culture | |
| Tap water to make 1 liter | |
| n-paraffin cut $C_{10} - C_{20}$ | 16.5 |

The pH of the medium was adjusted to the optimum value selected by adding an aqueous solution of sodium hydroxide or potassium hydroxide while the medium was vigorously agitated with sterile aeration.

10 ml samples of medium taken from the fermenter at determined intervals of time made it possible to determine the respective concentrations of citric and isocitric acids excreted by the methods of: Marier and Boulet (J. Dairy Sci 41, 1683–1692 (1958) and Siebert (Methods of Anzymatic Analysis, New York, N.Y. 1963 page 313).

The following table shows the results obtained at the end of 160 hours culture and makes it possible to compare the performance of the non-sporulant diploid strain D 1805 with that of the parental haploid strains IFP 29 and ELF 30.

| Examples | Strains | Citric Acid g/l | Isocitric Acid g/l | Total (Citric + Isocitric Acid) |
|---|---|---|---|---|
| 2 | D 1805 | 147 | 90 | 237 |
| 3 | IFP 29 | 123 | 42.5 | 165.5 |
| 4 | ELF 30 | 79 | 51.5 | 130.5 |

Analysis of the results given in the above table shows that the production of citric acid and isocitric acid resulting from the use of a diploid *Candida Lipolytica* yeast are substantial in comparison with that obtained by the fermentation of the parental strains.

The application of the process of the present invention, in which a diploid *Candida Lipolytica* yeast is cultured in the presence of a suitable concentration of thiamin, while maintaining a pH between 2 and 7 by progressively adding an aqueous solution of sodium or potassium hydroxide, and in the presence of a cyanoacetic acid or of a derivative of this acid in order to increase the yield of this culture, provides the following advantages:

a marked increase of yields from the culture per unit of time;

An increase of excretion times (at maximum production rate) of the culture, and consequently the production of substantial mounts of citric and isocitric acids.

What is claimed is:

1. In the production of citric and isocitric acids by fermentation of a nutrient medium by a *Candida lipolytic* yeast, said medium containing a hydrocarbon substrate as a source of carbon, substances which are sources of nitrogen, mineral compounds, and thiamin, the improvements which consist in employing a diploid *Candida lipolytica* yeast in a nutrient medium having a pH of between 2 and 7 and containing between 200 micrograms and 10 milligrams of thiamin per liter.

2. The method of claim 1, wherein the pH of the medium is between 3 and 6.

3. The method of claim 1, wherein the pH of the medium is maintained by including in said medium a non-nitrogen containing base selected from the group consisting of sodium hydroxide and potassium hydroxide.

4. The method of claim 1, in which cyanoacetic acid is included in the medium.

* * * * *

UNITED STATES PATENT OFFICE
CERTIFICATE OF CORRECTION

Patent No. 3,997,399      Dated December 14, 1976

Inventor(s) Paul Maldonado & Max Charpentier

It is certified that error appears in the above-identified patent and that said Letters Patent are hereby corrected as shown below:

Col. 4, Lines 18 and 19: The heading "Characteristics of Diploid Strains Obtained" has been omitted.

Signed and Sealed this

Twenty-second Day of November 1977

[SEAL]

Attest:

RUTH C. MASON
*Attesting Officer*

LUTRELLE F. PARKER
*Acting Commissioner of Patents and Trademarks*